(12) United States Patent
Kim et al.

(10) Patent No.: US 11,413,305 B2
(45) Date of Patent: Aug. 16, 2022

(54) **USE OF AGAR-DERIVED OLIGOSACCHARIDES FOR INHIBITING GROWTH OF *STAPHYLOCOCCUS***

(71) Applicant: Korea University Research and Business Foundation, Seoul (KR)

(72) Inventors: Kyoung Heon Kim, Seoul (KR); Jungwoo Yang, Seoul (KR); Ju Hwan Song, Seoul (KR); Sora Yu, Gyeonggi-do (KR)

(73) Assignee: Korea University Research and Business Foundation, Seoul (KR)

( * ) Notice: Subject to any disclaimer, the term of this patent is extended or adjusted under 35 U.S.C. 154(b) by 138 days.

(21) Appl. No.: 16/767,928

(22) PCT Filed: Nov. 20, 2018

(86) PCT No.: PCT/KR2018/014236
§ 371 (c)(1),
(2) Date: May 28, 2020

(87) PCT Pub. No.: WO2019/107820
PCT Pub. Date: Jun. 6, 2019

(65) Prior Publication Data
US 2021/0369765 A1 Dec. 2, 2021

(30) Foreign Application Priority Data
Nov. 28, 2017 (KR) .................. 10-2017-0160753

(51) Int. Cl.

| | | |
|---|---|---|
| *A61K 31/729* | (2006.01) | |
| *A23K 20/163* | (2016.01) | |
| *A23K 20/195* | (2016.01) | |
| *A23L 33/10* | (2016.01) | |
| *A23L 33/125* | (2016.01) | |
| *A61P 31/04* | (2006.01) | |
| *A61K 8/60* | (2006.01) | |
| *A61K 8/73* | (2006.01) | |
| *A61K 31/7016* | (2006.01) | |
| *A61K 31/702* | (2006.01) | |
| *A61Q 17/00* | (2006.01) | |

(52) U.S. Cl.
CPC .......... *A61K 31/729* (2013.01); *A23K 20/163* (2016.05); *A23K 20/195* (2016.05); *A23L 33/125* (2016.08); *A23L 33/127* (2016.08); *A61K 8/60* (2013.01); *A61K 8/602* (2013.01); *A61K 8/73* (2013.01); *A61K 31/702* (2013.01); *A61K 31/7016* (2013.01); *A61P 31/04* (2018.01); *A61Q 17/005* (2013.01); *A23V 2002/00* (2013.01)

(58) Field of Classification Search
None
See application file for complete search history.

(56) References Cited

U.S. PATENT DOCUMENTS

2009/0092565 A1    4/2009 Koyama et al.
2018/0055872 A1*   3/2018 Lee ................ C12Y 207/01107

FOREIGN PATENT DOCUMENTS

| JP | 2002-029952 A | 1/2002 | |
|---|---|---|---|
| KR | 10-2016-0083329 A | 7/2016 | |
| KR | 10-2017-0044945 A | 4/2017 | |
| WO | WO-2008079339 A2 * | 7/2008 | ........... C07D 265/02 |

OTHER PUBLICATIONS

Yun, E. J., Lee, A. R., Kim, J. H., Cho, K. M., & Kim, K. H. (2016). 3, 6-Anhydro-l-galactose, a rare sugar from agar, a new anticariogenic sugar to replace xylitol. Food chemistry, 221, 976-983. (Year: 2016).*

Yun, E. J., Yu, S., & Kim, K. H. (2017). Current knowledge on agarolytic enzymes and the industrial potential of agar-derived sugars. Applied microbiology and biotechnology, 101(14), 5581-5589. (Year: 2017).*

Jeong-Hwa Hong et al., "Antibacterial Activity of Agarooligosaccharides Produced by ß-Agarase from Bacillus cereus ASK 202", Journal of Food Hygiene and Safety, 2000, pp. 277-281, vol. 15, No. 4.

International Search Report for PCT/KR2018/014236 dated, Feb. 25, 2019 (PCT/ISA/210).

* cited by examiner

*Primary Examiner* — Dale R Miller
(74) *Attorney, Agent, or Firm* — Sughrue Mion, PLLC (57) ABSTRACT

The present invention relates to a use of agar-derived oligosaccharides for inhibiting the growth of *Staphylococcus*. More specifically, the present invention provides, as a material for medicine, food, cosmetics and the like, a use of agar-derived agarooligosaccharides, agarobiose or AHG, which have an effect of inhibiting the growth of *Staphylococcus* or killing the same.

4 Claims, 10 Drawing Sheets

USE OF AGAR-DERIVED OLIGOSACCHARIDES FOR INHIBITING GROWTH OF *STAPHYLOCOCCUS*

CROSS REFERENCE TO RELATED APPLICATIONS

This application is a National Stage of International Application No. PCT/KR2018/014236 filed Nov. 20, 2018, claiming priority based on Korean Patent Application No. 10-2017-0160753, filed Nov. 28, 2017.

BACKGROUND

1. Field of the Invention

The present invention relates to a use of agar-derived oligosaccharides having an effect of inhibiting the growth of *Staphylococcus* and killing the same.

2. Discussion of Related Art

The rapid generation and spread of pathogenic bacteria resistant to existing antibiotics is causing problems worldwide, and in particular, infections caused by *Staphylococcus* are a major part of these problems. *Staphylococcus aureus* is the most commonly found pathogen on skin and wound infections, and its infections range from relatively mild rashes to pneumonia, endocarditis, sepsis, and osteomyelitis. In addition, it is very difficult to treat staphylococcal infections because the staphylococci form biofilms and thereby evade hosts' immune functions, cause chronic infections, and interfere with wound healing, and the development of resistance to beta-lactam based antibiotics such as penicillin and, furthermore, the development of resistance to vancomycin are major obstacles to the treatment of staphylococcal infections. According to a report, about 11,000 people die in the United States each year from methicillin-resistant *Staphylococcus aureus* (MRSA) infections. In order to overcome this problem, in recent years, synthetic peptides having a short chain structure which are relatively harmless to the human body, oligosaccharides derived from plants, and the like have been studied as alternative anti-staphylococcal substances.

SUMMARY OF THE INVENTION

An object of the present invention is to provide, as inhibitors of *Staphylococcus* in industrial fields such as medicine, cosmetics, food, and the like, a use of agarooligosaccharides, agarobiose, and 3,6-anhydro-L-galactose (a non-reducing sugar, hereinafter referred to as "AHG") which are derived from agar, edible, and harmless to the human body.

To achieve the object, the present invention provides an antibacterial composition for inhibiting *Staphylococcus*, which includes one or more selected from the group consisting of an agarooligosaccharide, agarobiose, and AHG, wherein the agarooligosaccharide is a mixture of two or more selected from among agarobiose, agarotetraose, agarohexaose, and agarooctaose.

The present invention also provides a method of inhibiting the growth of *Staphylococcus* or killing the same, which includes contacting at least one type of *Staphylococcus* with an effective amount of one or more selected from the group consisting of an agarooligosaccharide, agarobiose, and AHG, wherein the agarooligosaccharide is a mixture of two or more selected from the group consisting of agarobiose, agarotetraose, agarohexaose, and agarooctaose.

The present invention also provides a pharmaceutical composition for preventing or treating a staphylococcal infectious disease, which includes one or more selected from the group consisting of an agarooligosaccharide, agarobiose, and AHG, wherein the agarooligosaccharide is a mixture of two or more selected from the group consisting of agarobiose, agarotetraose, agarohexaose, and agarooctaose.

The present invention provides a method of preventing or treating a staphylococcal infectious disease, which includes administering an effective amount of one or more selected from the group consisting of an agarooligosaccharide, agarobiose, and AHG to a subject in need thereof, wherein the agarooligosaccharide is a mixture of two or more selected from the group consisting of agarobiose, agarotetraose, agarohexaose, and agarooctaose.

The staphylococcal infectious disease may be a disease selected from among an abscess, acne, dermatitis, pneumonia, endocarditis, sepsis, osteomyelitis, osteoarthritis, bacteremia, toxic shock syndrome, food poisoning, hyperthermia, edema, mastitis, and enterocolitis caused by an infection by *Staphylococcus aureus* (*S. aureus*), *Staphylococcus epidermidis* (*S. epidermidis*), or *Staphylococcus pyogenes* (*S. pyogenes*).

The present invention also provides an antibacterial cosmetic composition effective against *Staphylococcus*, which includes one or more selected from the group consisting of an agarooligosaccharide, agarobiose, and AHG, wherein the agarooligosaccharide is a mixture of two or more selected from the group consisting of agarobiose, agarotetraose, agarohexaose, and agarooctaose.

The present invention also provides an antibacterial food composition effective against *Staphylococcus*, which includes one or more selected from the group consisting of an agarooligosaccharide, agarobiose, and AHG, wherein the agarooligosaccharide is a mixture of two or more selected from the group consisting of agarobiose, agarotetraose, agarohexaose, and agarooctaose.

The present invention also provides an antibacterial animal feed composition effective against *Staphylococcus*, which includes one or more selected from the group consisting of an agarooligosaccharide, agarobiose, and AHG, wherein the agarooligosaccharide is a mixture of two or more selected from the group consisting of agarobiose, agarotetraose, agarohexaose, and agarooctaose.

The present invention also provides a disinfectant effective against *Staphylococcus*, which includes one or more selected from the group consisting of an agarooligosaccharide, agarobiose, and AHG, wherein the agarooligosaccharide is a mixture of two or more selected from the group consisting of agarobiose, agarotetraose, agarohexaose, and agarooctaose.

The present invention also provides an antibacterial adjuvant for killing *Staphylococcus*, which includes one or more selected from the group consisting of an agarooligosaccharide, agarobiose, and AHG, wherein the agarooligosaccharide is a mixture of two or more selected from the group consisting of agarobiose, agarotetraose, agarohexaose, and agarooctaose.

Here, the *Staphylococcus* includes *S. aureus*, *S. epidermidis*, or *S. pyogenes*.

The present invention has an effect of providing, as a material for medicine, food, cosmetics, and the like, a use of an agarooligosaccharide, agarobiose, or AHG which is derived from agar and has an effect of inhibiting the growth of *Staphylococcus* and killing the same.

DETAILED DESCRIPTION OF EXEMPLARY EMBODIMENTS

Hereinafter, the configuration of the present invention will be described in detail.

One aspect of the present invention provides an antibacterial composition for inhibiting Staphylococcus, which includes one or more selected from the group consisting of an agarooligosaccharide, agarobiose, and AHG, wherein the agarooligosaccharide is a mixture of two or more selected from the group consisting of agarobiose, agarotetraose, agarohexaose, and agarooctaose.

Another aspect of the present invention provides a method of inhibiting the growth of Staphylococcus or killing the same, which includes contacting at least one type of Staphylococcus with an effective amount of one or more selected from the group consisting of an agarooligosaccharide, agarobiose, and AHG, wherein the agarooligosaccharide is a mixture of two or more selected from the group consisting of agarobiose, agarotetraose, agarohexaose, and agarooctaose.

According to one embodiment of the present invention, an agarooligosaccharide, agarobiose, or AHG, which is derived from agar, has an effect of inhibiting the growth of Staphylococcus or killing the same. Specifically, the antibacterial effect against Staphylococcus decreases in the order of agarobiose, a mixture of DP2+DP4+DP6+DP8, a mixture of DP4+DP6+DP8, and AHG. On the other hand, neoagarobiose, which is formed by the α-1,3 bond of AHG-Gal, and galactose do not show an antibacterial effect against Staphylococcus.

The agarooligosaccharide may be a mixture of two or more selected from the group consisting of agarobiose, agarotetraose, agarohexaose, and agarooctaose obtained through a known method such as the enzymatic hydrolysis of agar (e.g., by using agarase) or the acid hydrolysis of agar (e.g., treatment with strong or weak acids).

The agarobiose may be obtained from a mixture of agarooligosaccharides having various degrees of polymerization through purification using size-exclusion chromatography and used.

The AHG may be obtained by carrying out isolation and purification through a known method such as the enzymatic hydrolysis of agar (e.g., by using agarase or other agarobiose hydrolases) or a combination of acid hydrolysis and enzymatic hydrolysis of agar (e.g., by using agarase or other agarobiose hydrolases after treatment with strong or weak acids).

Here, the Staphylococcus may include S. aureus, S. epidermidis, S. pyogenes, or the like.

S. aureus is a Gram-positive, facultative anaerobic bacterium that forms a cell mass (lump) as it grows, and is generally present on the skin and nasal surfaces of healthy humans or livestock. S. aureus causes food poisoning by producing a heat-resistant exotoxin, and causes purulent infections by evading the defenses of infected host cells by secreting phagocyte-killing toxins (e.g., leukocidin), hemolytics, coagulation enzymes, and the like. Recently, antibiotic-resistant bacteria that are resistant to most antibiotics have appeared in hospitals and the like, causing serious societal problems.

As described above, since the agarooligosaccharide, agarobiose, and AHG have an effect of inhibiting the growth of Staphylococcus and killing the same, they are usable as an agent for the prevention or treatment of a staphylococcal infectious disease.

Therefore, still another aspect of the present invention provides a pharmaceutical composition for preventing or treating a staphylococcal infectious disease, which includes one or more selected from the group consisting of an agarooligosaccharide, agarobiose, and AHG, wherein the agarooligosaccharide is a mixture of two or more selected from the group consisting of agarobiose, agarotetraose, agarohexaose, and agarooctaose.

Yet another aspect of the present invention provides a method of preventing or treating a staphylococcal infectious disease, which includes administering an effective amount of one or more selected from the group consisting of an agarooligosaccharide, agarobiose, and AHG to a subject in need thereof, wherein the agarooligosaccharide is a mixture of two or more selected from the group consisting of agarobiose, agarotetraose, agarohexaose, and agarooctaose.

The staphylococcal infectious disease may be a disease caused by an infection by S. aureus, S. epidermidis, or S. pyogenes, for example, dermatitis, such as abscess, acne, localized sofa dermatitis, allergic contact dermatitis, poison ivy dermatitis, atopic dermatitis, seborrheic dermatitis, systemic exfoliative dermatitis, congestive dermatitis, peripheral dermatitis, or psoriasis; osteoarthritis; bacteremia; pneumonia; toxic shock syndrome; food poisoning; hyperthermia; sepsis; edema; mastitis; or enterocolitis, but the present invention is not limited thereto.

As used herein, the term "prevention" refers to any action that inhibits or delays the onset of a staphylococcal infectious disease by administering a pharmaceutical composition of the present invention to an individual.

As used herein, the term "treatment" refers to any action that alleviates or improves the symptoms of a staphylococcal infectious disease by administering a pharmaceutical composition of the present invention to an individual.

As used herein, the term "effective amount" refers to the amount of a compound exhibiting a therapeutic effect against a staphylococcal infectious disease.

As used herein, the term "subject in need thereof" refers to a mammal infected by a microorganism that shortens the life of a mammal by threatening the life of the mammal or compromising the health of the mammal.

The pharmaceutical composition of the present invention may further include a pharmaceutically acceptable carrier.

The pharmaceutically acceptable carrier may include a carrier and a vehicle commonly used in the pharmaceutical field, and specifically, may include an ion exchange resin, alumina, aluminum stearate, lecithin, a serum protein (e.g., human serum albumin), a buffer material (e.g., various phosphates, glycine, sorbic acid, potassium sorbate, or a partial glyceride mixture of saturated vegetable fatty acids), water, a salt, an electrolyte (e.g., protamine sulfate, disodium hydrogen phosphate, potassium hydrogen phosphate, sodium chloride, or a zinc salt), colloidal silica, magnesium trisilicate, polyvinylpyrrolidone, a cellulose-based substrate, polyethylene glycol, sodium carboxymethylcellulose, a polyarylate, a wax, polyethylene glycol, lanolin, or the like, but the present invention is not limited thereto.

In addition, the pharmaceutical composition of the present invention may further include a lubricant, a wetting agent, an emulsifier, a suspending agent, a preservative, or the like in addition to the above-described components.

In one embodiment, the pharmaceutical composition of the present invention may be formulated into a variety of formulations suitable for oral administration or parenteral administration and used.

Non-limiting examples of the formulation for oral administration include troches, lozenges, tablets, aqueous suspensions, oily suspensions, preparation powders, granules, emulsions, hard capsules, soft capsules, syrups, elixirs, and the like.

In addition, in order to formulate the pharmaceutical composition of the present invention for oral administration, a binder such as lactose, saccharose, sorbitol, mannitol, starch, amylopectin, cellulose, or gelatin, an excipient such as dicalcium phosphate, a disintegrant such as corn starch or sweet potato starch, a lubricant such as magnesium stearate, calcium stearate, sodium stearyl fumarate, or polyethylene glycol wax, a sweetener, a fragrance, a syrup, and the like may also be used.

Furthermore, in the case of capsules, a liquid carrier such as fatty oil may also be used in addition to the above-described materials.

Non-limiting examples of the formulation for parenteral administration include injection solutions, suppositories, respiratory inhalation powders, spray aerosols, oral sprays, mouthwashes, toothpastes, ointments, application powders, oils, creams, and the like.

In order to formulate the pharmaceutical composition of the present invention for parenteral administration, a sterilized aqueous solution, a non-aqueous solvent, a suspending agent, an emulsion, a freeze-dried preparation, an external preparation, and the like may be used, and as the non-aqueous solvent or the suspending agent, propylene glycol, polyethylene glycol, a vegetable oil such as olive oil, an injectable ester such as ethyl oleate, or the like may be used.

In addition, more specifically, when the pharmaceutical composition of the present invention is formulated into an injectable solution, the pharmaceutical composition of the present invention may be prepared as a solution or suspension by mixing with a stabilizer or buffer in water and formulated for unit administration in ampoules or vials. In addition, when the pharmaceutical composition of the present invention is formulated as an aerosol, a propellant or the like may be added along with additives so that the water-dispersed concentrate or wet powder is dispersed.

In addition, when the pharmaceutical composition of the present invention is formulated as an ointment, a cream, or the like, an animal oil, a vegetable oil, a wax, paraffin, starch, tragacanth, a cellulose derivative, polyethylene glycol, silicone, bentonite, silica, talc, zinc oxide, or the like may be used as a carrier for the formulation.

The pharmaceutically effective amount and effective dose of the pharmaceutical composition of the present invention may be varied depending on the method of formulating the composition, mode of administration, time of administration, route of administration, and/or the like, and may be varied depending on a variety of factors including the type and extent of a reaction to be achieved by the administration of the pharmaceutical composition of the present invention, the type, age, weight, general health conditions, sex, diet, and excretion rate of the subject to be administered, symptoms or severity of disease, and components of additional drug compositions also administered to the subject at the time of administering the pharmaceutical composition of the present invention or at different times, and similar factors well known in the pharmaceutical field, and one of ordinary skill in the art can readily determine and prescribe an effective dose for the desired treatment. The pharmaceutical composition of the present invention may be administered once a day or in divided doses. Therefore, the dosage of the present specification is not intended to limit the scope of the invention in any way.

The route and mode of administration of the pharmaceutical composition of the present invention may be independent of each other and are not limited in any way, and any route and mode of administration may be used as long as it enables the pharmaceutical composition to reach the desired site. The pharmaceutical composition may be administered orally or parenterally.

The mode of parenteral administration may be, for example, intravenous administration, intraperitoneal administration, intramuscular administration, transdermal administration, or subcutaneous administration, and a method of applying or spraying the pharmaceutical composition on a diseased site or inhaling the same may also be used, but the present invention is not limited thereto.

The pharmaceutical composition of the present invention is preferably administered orally or by injection.

Yet another aspect of the present invention provides an antibacterial cosmetic composition effective against *Staphylococcus*, which includes one or more selected from the group consisting of an agarooligosaccharide, agarobiose, and AHG, wherein the agarooligosaccharide is a mixture of two or more selected from the group consisting of agarobiose, agarotetraose, agarohexaose, and agarooctaose.

The cosmetic composition of the present invention may be variously used for preventing or alleviating a staphylococcal infectious skin disease.

The cosmetic composition of the present invention may include: a water-soluble vitamin such as vitamin B1, vitamin B2, vitamin B6, pyridoxine, pyridoxine hydrochloride, vitamin B12, pantothenic acid, nicotinic acid, nicotinic acid amide, folic acid, vitamin C, or vitamin H; an oil-soluble vitamin such as vitamin A, carotene, vitamin D2, vitamin D3, or vitamin E (D1-α-tocopherol or D-α-tocopherol); a polymer peptide such as collagen, hydrolyzed collagen, gelatin, elastin, hydrolyzed elastin, or keratin; a polymer polysaccharide such as hydroxyethyl cellulose, xanthan gum, sodium hyaluronate, chondroitin sulfate, or a salt thereof (e.g., sodium salt); a sphingolipid such as a ceramide, phytosphingosine, or a sphingoglycolipid; or a seaweed extract such as a brown algae extract, a red algae extract, or a green algae extract.

In the cosmetic composition of the present invention, additional ingredients that are commonly used in a cosmetic composition may be included in addition to the above-described essential components as necessary. Examples of the additional ingredients that may be used include a fat/oil ingredient, a moisturizer, an emollient, a surfactant, an organic or inorganic pigment, an organic powder, a UV absorber, a preservative, a bactericide, an antioxidant, a plant extract, a pH adjusting agent, an alcohol, a dye, a fragrance, a blood circulation accelerator, a cooling agent, an antiperspirant, and purified water. Examples of the fat/oil ingredient include an ester-based oil, a hydrocarbon-based oil, a silicone-based oil, a fluorine-based oil, an animal fat, and a vegetable oil.

However, the additional ingredients that may be used are not limited thereto, and any of the above-described ingredients may be used within a range not impairing the objectives and effects of the present invention.

The cosmetic composition of the present invention may take the form of a solution, an emulsion, a viscous mixture, or the like.

Examples of the ingredients included in the cosmetic composition of the present invention may include ingredients commonly used in cosmetic compositions as active ingredients, such as conventional adjuvants (e.g., stabilizers, solubilizers, vitamins, pigments, and fragrances) and conventional carriers.

The cosmetic composition of the present invention may be prepared as any of the formulations conventionally prepared in the art and, for example, may be formulated as a skin lotion, a skin softener, a skin toner, a milk lotion, an astringent, a lotion, a moisturizing lotion, a nourishing lotion, a massage cream, a nourishing cream, a moisturizing cream, a hand cream, a foundation, a serum, a nourishing serum, a pack, a soap, a cleansing foam, a cleansing lotion, a cleansing cream, a hair lotion, a hair tonic, a hair serum, a hair shampoo, a hair conditioner, a hair treatment, a body lotion, or a body cleanser.

Yet another aspect of the present invention provides an antibacterial food composition effective against *Staphylococcus*, which includes one or more selected from the group consisting of an agarooligosaccharide, agarobiose, and AHG, wherein the agarooligosaccharide is a mixture of two or more selected from the group consisting of agarobiose, agarotetraose, agarohexaose, and agarooctaose.

The food composition of the present invention may be used as a health functional food, a food additive, or a dietary supplement.

When the agarooligosaccharide, agarobiose, or AHG of the present invention is used as a food additive, it may be suitably used according to a conventional method, for example, by being added as is or being mixed with other food or food ingredients and used.

In addition, the usage amount of the agarooligosaccharide, agarobiose, or AHG may be suitably adjusted according to the purpose of use (e.g., prevention, health care or therapeutic treatment), and is preferably 0.01 to 95% by weight and more preferably 0.1 to 80% by weight relative to the total weight of the food composition. When the content of the agarooligosaccharide, agarobiose, or AHG is less than 0.01 wt %, the efficiency of administration may be lowered, and when the content of the agarooligosaccharide, agarobiose, or AHG is more than 95 wt %, there may be difficulty in formulation.

As a specific example, when producing food or beverages, the agarooligosaccharide, agarobiose, or AHG of the present invention is added in an amount of 15% or less by weight and preferably 10% or less by weight based on the raw material. On the other hand, for long-term intake for the purpose of health and hygiene promotion or health care, the agarooligosaccharide, agarobiose, or AHG of the present invention may be added in an amount less than the above-described range, and the active ingredient may also be used in an amount greater than the above-described range, since there is no problem in terms of safety.

The type of the above-described food is not particularly limited, and examples of foods to which the agarooligosaccharide, agarobiose, or AHG of the present invention may be added include meats, sausages, breads, chocolates, candies, snacks, confectioneries, pizzas, ramen, other noodles, gums, dairy products including ice creams, various soups, beverages, teas, drinks, alcoholic beverages, vitamin complexes, and all types of healthy foods in the ordinary sense.

When the food composition of the present invention is prepared as a beverage, it may contain additional components such as various flavoring agents or natural carbohydrates, like a conventional beverage. As the natural carbohydrate, a monosaccharide such as glucose or fructose, a disaccharide such as maltose or sucrose, a natural sweetener such as dextrin or cyclodextrin, a synthetic sweetener such as saccharin or aspartame, or the like may be used. The natural carbohydrate is used in an amount of 0.01 to 10% by weight and preferably 0.01 to 0.1% by weight relative to the total weight of the food composition of the present invention.

The food composition of the present invention may include various nutrients, vitamins, electrolytes, flavoring agents, coloring agents, pectic acid and salts thereof, alginic acid and salts thereof, organic acids, protective colloid thickeners, pH adjusting agents, stabilizers, preservatives, glycerin, alcohols, carbonating agents used in carbonated drinks, and the like, and may include the flesh of fruits for the production of natural fruit juices, fruit juice beverages, and vegetable beverages, but the present invention is not limited thereto. These ingredients may be used independently or in combination. The addition amounts of these additives are not particularly limited, and are preferably in the range of 0.01 to 0.1% by weight relative to the total weight of the food composition of the present invention. The food composition of the present invention is suitable for long-term intake for the purpose of health and hygiene promotion or health care because the long-term administration of the composition does not cause a problem in terms of safety.

Yet another aspect of the present invention provides an antibacterial animal feed composition effective against *Staphylococcus*, which includes one or more selected from the group consisting of an agarooligosaccharide, agarobiose, and AHG, wherein the agarooligosaccharide is a mixture of two or more selected from the group consisting of agarobiose, agarotetraose, agarohexaose, and agarooctaose.

The agarooligosaccharide, agarobiose, or AHG is preferably included in an amount of 0.01 to 95% by weight and more preferably included in an amount of 1 to 80% by weight relative to the total weight of the animal feed composition. When the content of the agarooligosaccharide, agarobiose, or AHG is less than 0.01 wt %, the efficiency of administration may be lowered, and when the content of the agarooligosaccharide, agarobiose, or AHG is more than 95 wt %, there may be difficulty in formulation.

The animal feed composition of the present invention including the agarooligosaccharide, agarobiose, or AHG as an active ingredient may be fed to livestock to prevent or improve diseases caused by pathogenic bacteria in animals.

The animal subject to which the animal feed composition is administered may be a ruminant or a non-ruminant but is preferably a ruminant such as a cow, a camel, a deer, or a giraffe.

The animal feed composition of the present invention may further include, in addition to the active ingredient, an organic acid such as citric acid, fumaric acid, adipic acid, lactic acid, or malic acid, a phosphate such as sodium phosphate, potassium phosphate, acidic pyrophosphate, or polyphosphate (polymeric phosphate), or a natural antioxidant such as a polyphenol, catechin, alpha-tocopherol, a rosemary extract, vitamin C, a green tea extract, a licorice extract, chitosan, tannic acid, or phytic acid commonly used in animal feed compositions.

In addition, the animal feed composition may further include an auxiliary component such as an amino acid, an inorganic salt, a vitamin, an antibiotic, an antibacterial material, an antioxidant, an antifungal enzyme, or a living microbial agent. Specifically, examples of the auxiliary component include grains (e.g., milled or crushed wheat, oat, barley, corn, rice, etc.), vegetable protein feed (e.g., feed including rapeseed, soybean, sunflower, etc. as main ingredients), animal protein feed (e.g., blood, meat, bone, fish, etc.), sugar and dairy products (e.g., dry ingredients consisting of various powdered milk or whey powders), lipids (e.g., an animal fat, a vegetable fat, etc.), nutritional supplements, digestive and absorption enhancers, growth promoters, and disease prevention agents.

The animal feed composition may be administered alone to an animal or may be administered in combination with other feed additives in an edible carrier. In addition, the animal feed composition may be mixed with feed as a top dressing for the feed or may be easily administered in combination with the feed as a separate additive or a separate oral formulation. The dosage of the animal feed composition may be suitably adjusted to a single daily intake amount or divided daily intake amounts commonly administered in the art.

Yet another aspect of the present invention provides a disinfectant effective against *Staphylococcus*, which includes one or more selected from the group consisting of an agarooligosaccharide, agarobiose, and AHG, wherein the agarooligosaccharide is a mixture of two or more selected from the group consisting of agarobiose, agarotetraose, agarohexaose, and agarooctaose.

Yet another aspect of the present invention provides an antibacterial adjuvant for killing *Staphylococcus*, which includes one or more selected from the group consisting of an agarooligosaccharide, agarobiose, and AHG, wherein the agarooligosaccharide is a mixture of two or more selected from the group consisting of agarobiose, agarotetraose, agarohexaose, and agarooctaose.

Hereinafter, the present invention will be described in more detail through exemplary embodiments of the present invention, but the scope of the present invention is not limited by the exemplary embodiments described below.

<Example 1> Growth Inhibition Experiment of Staphylococci by Agarooligosaccharide

*S. aureus* (KCCM12256) and *S. epidermidis* (KCCM35494) distributed from the Korean Culture Center of Microorganisms were used. The medium for Staphylococci used a M9 salt supplemented with 2 mM $MgSO_4$, 0.1 mM $CaCl_2$), 1% (w/v) glucose, 1% (w/v) casamino acid, 1 mM thiamine HCl, and 0.05 mM nicotinamide. The thiamine-HCl solution and the nicotinamide solution were filtered using a filter having a pore size of 0.2 μm, and the other components were autoclaved at 121° C. for 15 minutes and used. After mixing the medium components according to their respective concentrations, the mixture was filtered again using a filter having a pore size of 0.2 μm.

An agarooligosaccharide, which was a mixture of agarobiose (DP2), agarotetraose (DP4), agarohexaose (DP6), agarooctaose (DP8), and the like, was purchased from Takara Bio Inc. and used.

In the growth inhibition experiment, the *S. aureus* and the *S. epidermidis* were seed-cultured at 37° C. and 200 rpm for 24 hours and then subcultured. After incubation up to the mid-exponential phase ($OD_{600}$=2.5) through the subculture, the bacteria were inoculated into liquid media containing the agarooligosaccharide at concentrations of 0 mg/mL, 1 mg/mL, 2 mg/mL, and 4 mg/mL so that the initial absorbance (i.e., initial cell population) thereof at 600 nm was 0.01. Subsequently, each of the above was dispensed in 200 μl aliquots into a 96-well plate, and absorbance was measured while culturing the bacteria. The incubation and the absorbance measurement were performed using Synergy HTX Multi-Mode Reader commercially available from BioTek Instruments, Inc. The incubation was performed at 37° C. and 200 rpm, and the absorbance was measured at a wavelength of 600 nm.

Figure 1:
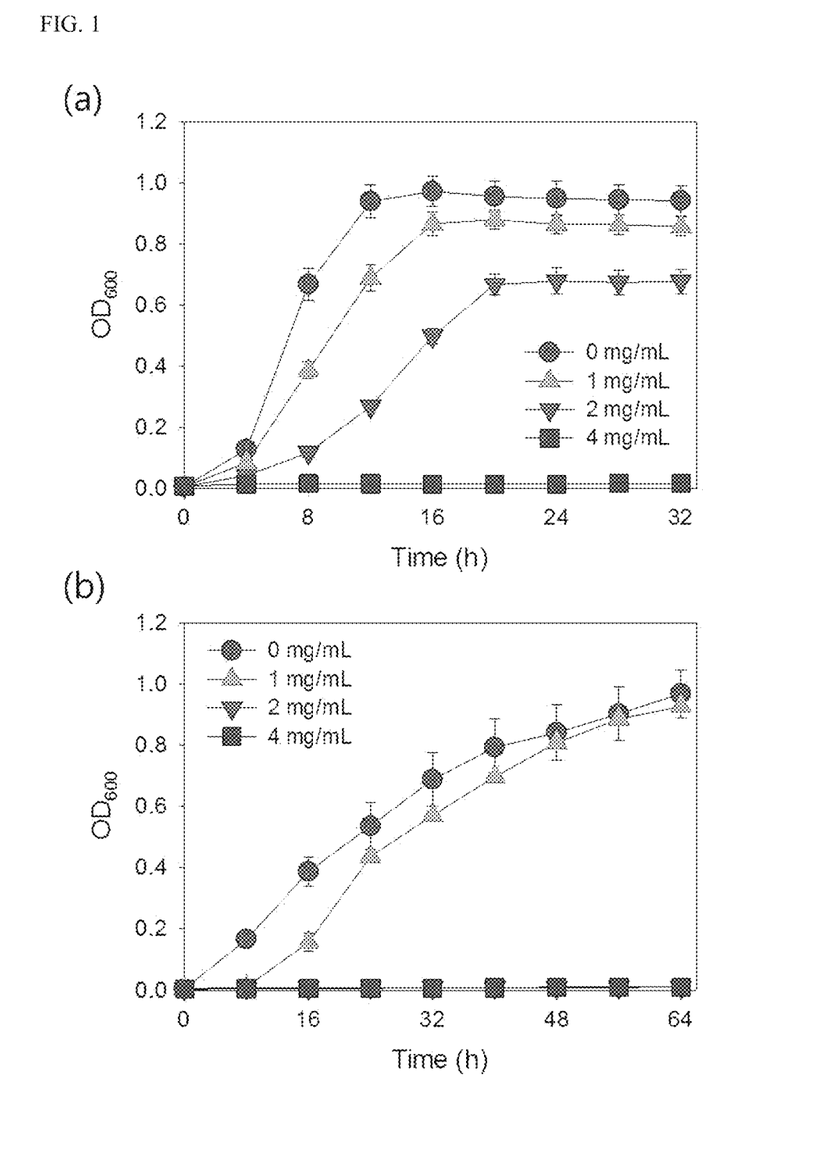
FIG. 1 shows the results of inhibiting the growth of (a) S. aureus and (b) S. epidermidis using an agarooligosaccharide which is a mixture of agarobiose, agarotetraose, agarohexaose, and agarooctaose.

As a result of culturing *S. aureus* and *S. epidermidis* at various agarooligosaccharide concentrations, it was observed that overall, the growth of Staphylococci decreased as the agarooligosaccharide concentration increased. In particular, it was confirmed that the growth of *S. aureus* and *S. epidermidis* was completely inhibited at agarooligosaccharide concentrations of 4 mg/mL and 2 mg/mL (FIG. 1).

<Example 2> Purification of Agarobiose

Figure 2:
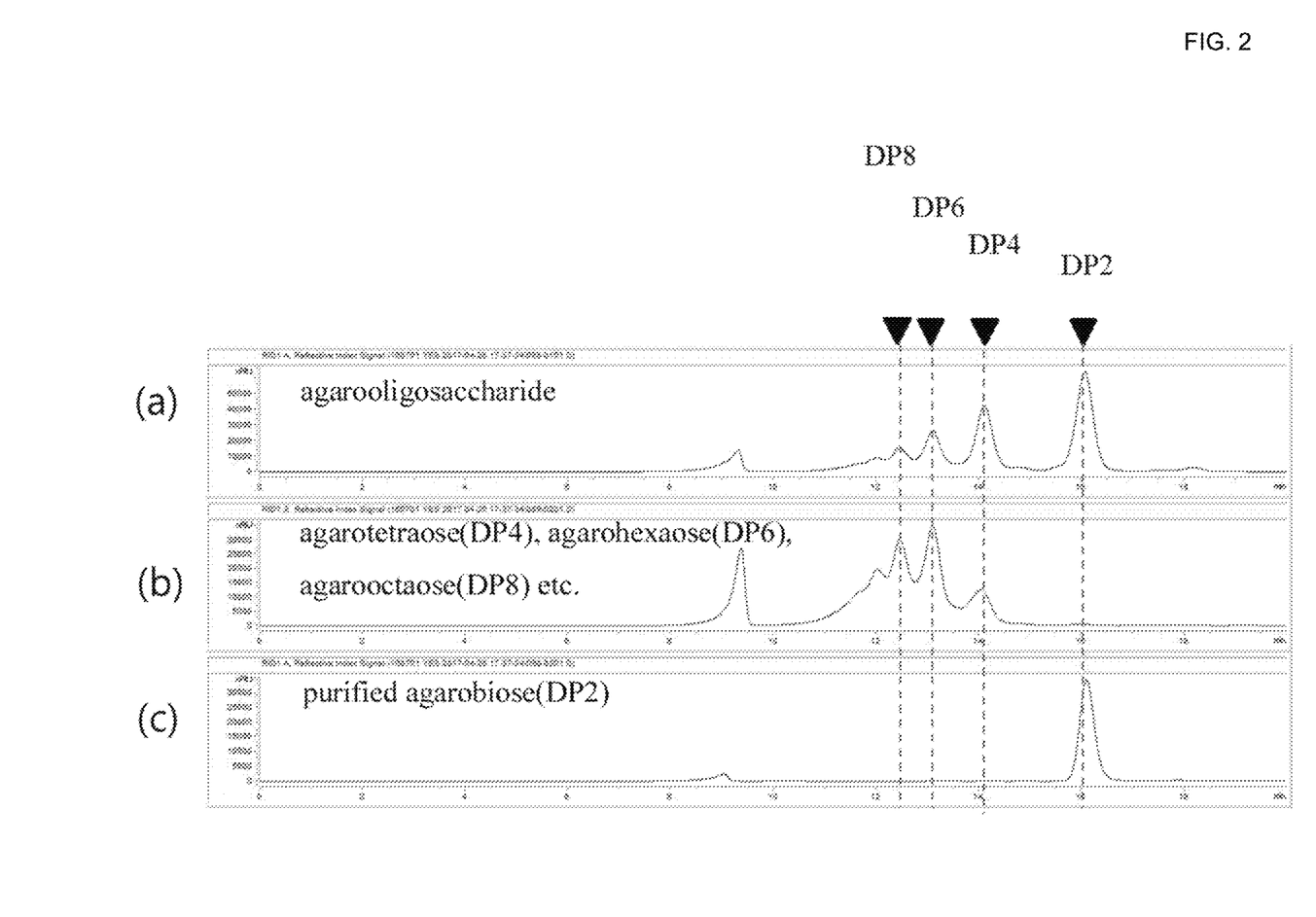
FIG. 2 shows the high-performance liquid chromatography (HPLC) analysis results of samples isolated by using size-exclusion chromatography. (a) Agarooligosaccharide which is a mixture of agarobiose, agarotetraose, agarohexaose, and agarooctaose, (b) Agarooligosaccharide which is a mixture of agarotetraose, agarohexaose, and agarooctaose, and (c) Agarobiose.

Following the confirmation of the growth inhibitory effect of the agarooligosaccharide against Staphylococci in Example 1, only pure agarobiose was obtained through purification using size-exclusion chromatography (FIG. 2).

The column used for purification was an XK 16/70 column (GE Healthcare Life Sciences) packed with a Bio-Gel P-2 Gel (Bio-Rad Laboratories, Inc). The Bio-Gel P-2 Gel, which is a size-exclusion resin, separated the agarooligosaccharide by size. The purity of the purified agarobiose was evaluated using high-performance liquid chromatography (HPLC). The HPLC column used for the analysis was a Shodex™ KS-802 column, and the analysis was carried out for 20 minutes at a flow rate of 0.5 mL/min using tertiary distilled water as a mobile phase.

<Example 3> Growth Inhibition Experiment of Staphylococci by Agarobiose

The inhibition of growth of Staphylococci was tested using the pure agarobiose obtained through isolation/purification in Example 2.

The growth inhibition test was carried out in the same manner as in Example 1, except that the agarooligosaccharide was replaced by agarobiose (1 or 2 mg/mL).

Figure 3:
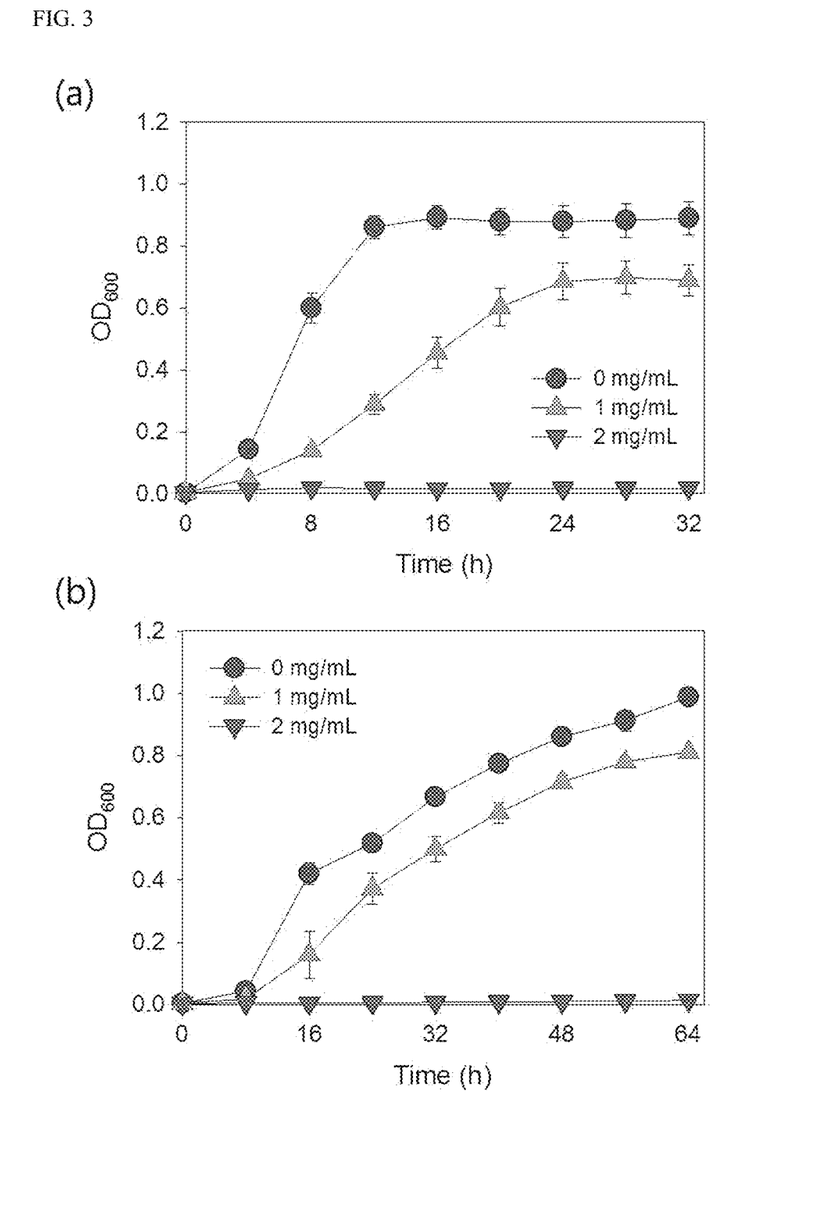
FIG. 3 shows the results of inhibiting the growth of (a) S. aureus and (b) S. epidermidis using agarobiose.

As shown in FIG. 3, it was confirmed that the growth of Staphylococci was more inhibited as the concentration of agarobiose increased, and particularly, was completely inhibited at a concentration of 2 mg/mL.

Figure 4:
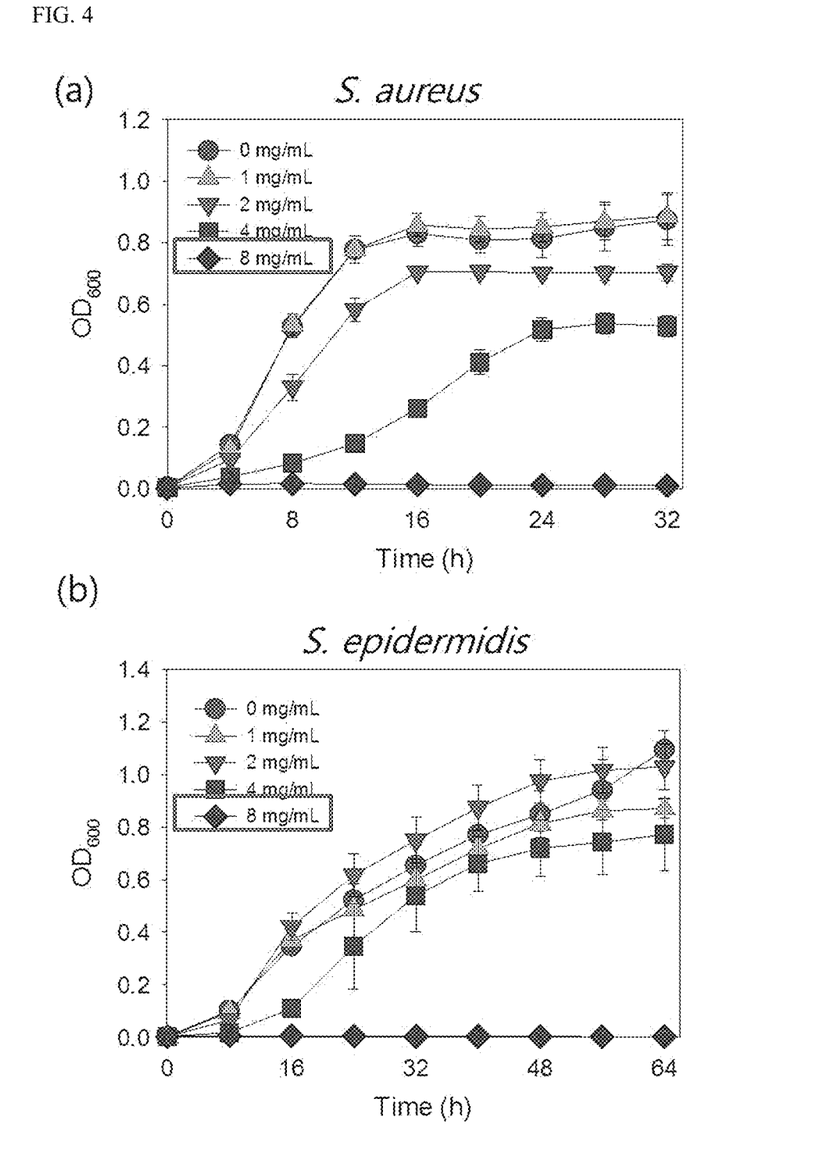
FIG. 4 shows the results of inhibiting the growth of (a) S. aureus and (b) S. epidermidis using an agarooligosaccharide excluding agarobiose (i.e., a mixture of agarotetraose, agarohexaose, and agarooctaose).

As a result of carrying out a staphylococcal growth inhibition test using an agarooligosaccharide mixture (DP4+DP6+DP8) excluding agarobiose, it was observed that as shown in FIG. 4, the growth of Staphylococci was more inhibited as the concentration of the agarooligosaccharide increased and was completely inhibited at a concentration of 8 mg/mL.

<Example 4> Growth Inhibition Experiment of Staphylococci Using Disk Diffusion Assay The disk diffusion assay is a common method of determining whether microbial growth is inhibited based on the diffusion of antibiotics in a disk. Accordingly, agarobiose was dispensed in an amount of 0 to 150 μg/disk on each disk to observe the growth of Staphylococci.

To this end, a solid medium for a disk diffusion assay having the same composition as in Example 1 was used, except that 1.5% agar was added to the liquid medium. The disks used in this experiment were paper disks commercially available from Advantec MFS (Tokyo, Japan), which had a thickness of 0.7 mm and a diameter of 10 mm. First, the disks were prepared such that they contained agarobiose in an aqueous state in amounts of 0, 50, 100, and 150 μg/disk. Subsequently, a staphylococcal culture was streaked on the provided solid medium using a sterile cotton swab so that the Staphylococci were evenly distributed on the medium, and the prepared disks were placed on the solid medium inoculated with the bacteria. Subsequently, after culturing the bacteria at 37° C. for 16 hours, it was observed that a zone of inhibition appeared.

Figure 5:
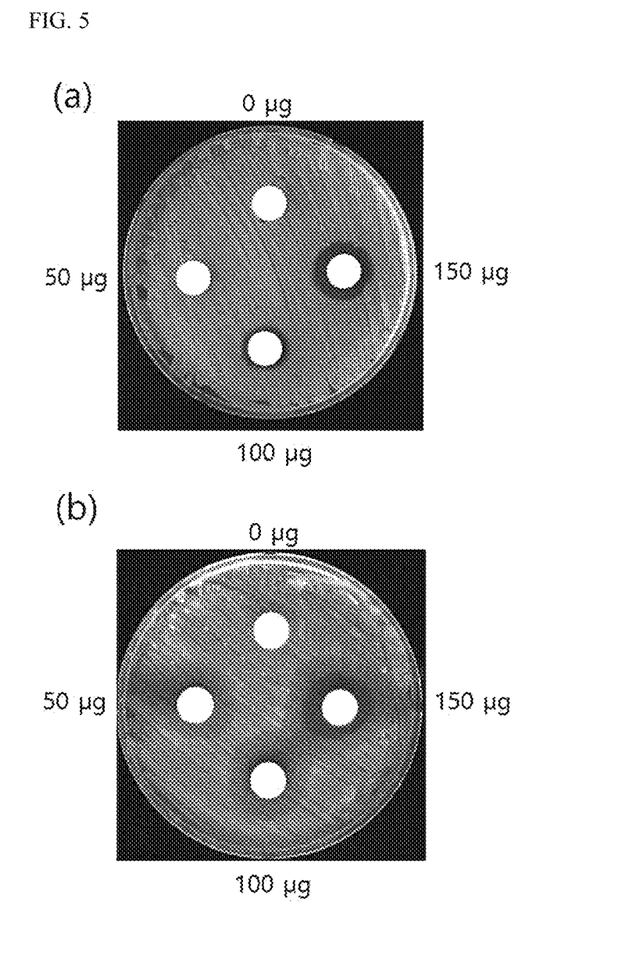
FIG. 5 shows disk diffusion assay results illustrating the inhibition of growth of (a) S. aureus and (b) S. epidermidis using agarobiose.

As shown in FIG. 5, based on the observation that Staphylococci did not grow at all at concentrations of 50 to 150 μg/disk, it was confirmed that agarobiose was an anti-staphylococcal substance.

<Example 5> Experiment for Observing Changes in Number of Viable Staphylococci According to Culture Time after Addition of Agarobiose In order to observe changes in staphylococcal growth according to culture time after the addition of agarobiose, the number of viable Staphylococci was monitored for 16 hours or 32 hours. To this end, the initial cell concentration was adjusted to an average of about $6.5 \times 10^6$ CFU/mL for both *S. aureus* and *S. epidermidis*, and the experiment was carried out at agarobiose concentrations of 0, 2, and 4 mg/mL.

The same culture conditions as in the method of Example 1 were applied, except that agarobiose concentrations of 0, 2, and 4 mg/mL were applied. At a working volume of 10 mL, the number of viable cells instead of absorbance was measured. To this end, the original sample was taken at each time point, diluted to $10^{-3}$ to $10^{-6}$ using 0.85% physiological saline, and then dispensed onto a trypticase soy agar (TSA; BD Bioscience, Franklin Lakes, N.J.) medium. After 16 to 24 hours, colony-forming unit (CFU)/mL was calculated and converted based on a dilution factor.

Figure 6:
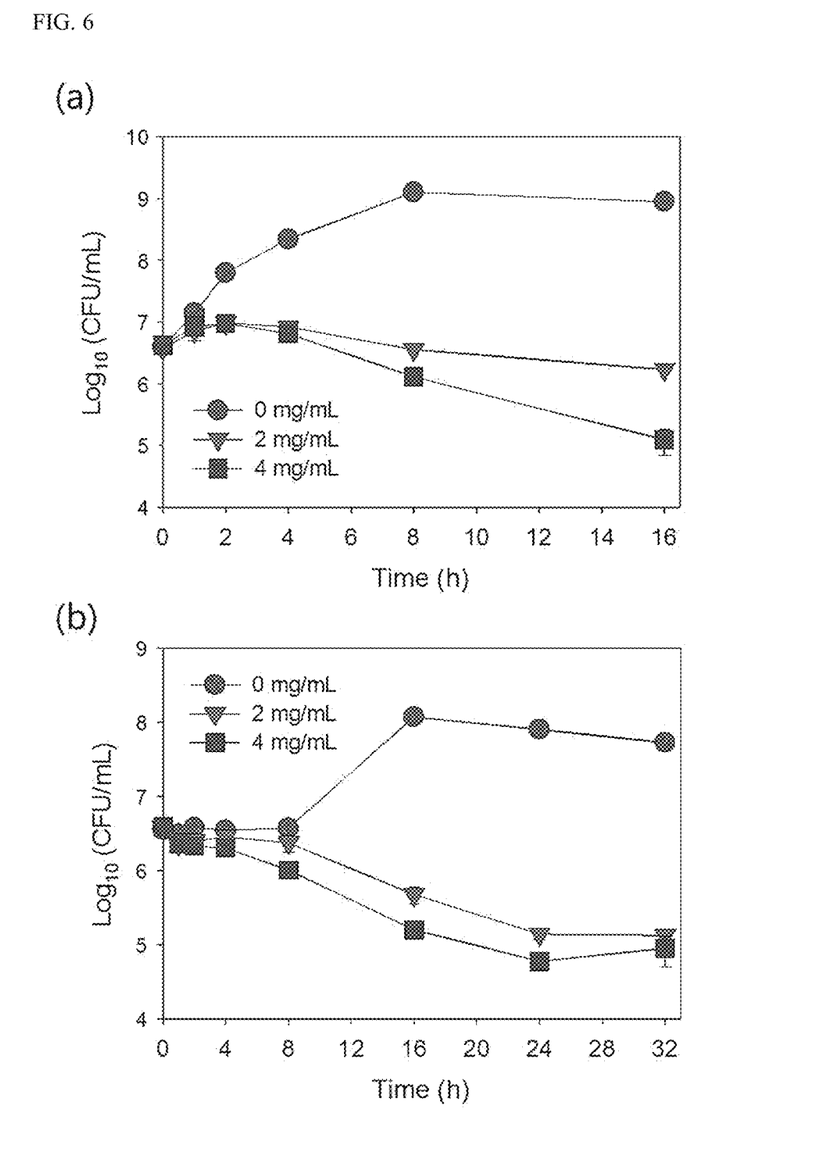
FIG. 6 shows the results of measuring the number of viable (a) S. aureus and (b) S. epidermidis over incubation times after addition of agarobiose.

As shown in FIG. 6, it was observed that in the absence of agarobiose, the two types of Staphylococci grew to about $10^8$ to $10^9$ CFU/mL after 8 to 16 hours, showing normal growth. On the other hand, at agarobiose concentrations of 2 mg/mL or more, it was observed that the growth of the two types of Staphylococci was inhibited. In particular, it was observed that at concentrations of 2 mg/mL and 4 mg/mL, after culturing for 16 to 32 hours, the number of viable cells decreased by a maximum of 1.5 $\log_{10}$ (CFU/mL) from the initial number of viable cells $6.5 \times 10^6$ CFU/mL.

<Example 6> Experiment for Observing Changes in *S. aureus* Cell Viability after Addition of Agarobiose (LIVE/DEAD Cell Viability Assay)

The effect of the addition of agarobiose on the survival of *S. aureus* was tested using an Invitrogen LIVE/DEAD BacLight bacterial viability kit. The LIVE/DEAD BacLight bacterial viability kit is commonly used to confirm cell survival through a two-color bacterial viability assay, where cells treated with two types of stains provided in the kit exhibit either green fluorescence or red fluorescence, which indicates living cells and dead cells, respectively. To this end, after adjusting the number of *S. aureus* in a liquid medium containing agarobiose at 2 mg/mL so that the absorbance at 600 nm was 0.5, the *S. aureus* was cultured at 37° C. and 200 rpm. At 0 and 8 hours after incubation, the cells were washed with 0.85% physiological saline, resuspended in PBS buffer, and stained in accordance with the kit's protocol. Equal volumes of SYTO® 9 and propidium iodide reagents included in the kit were added and then reacted for 15 minutes in the dark. The stained cells were observed with a confocal scanning laser microscope.

Figure 7:
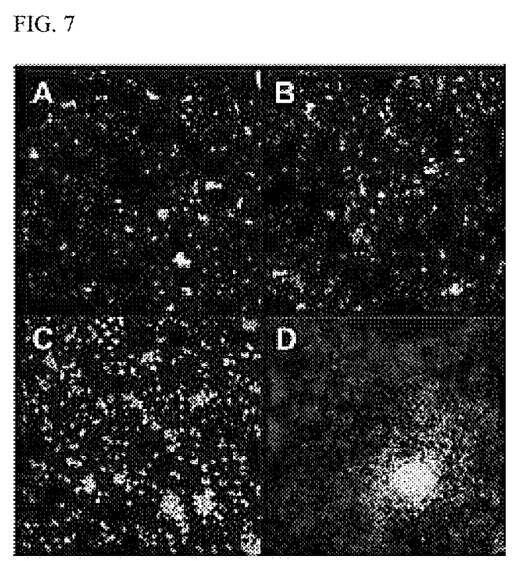
FIG. 7 shows the change in cell viability of S. aureus after the addition of agarobiose, wherein A is agarobiose-untreated cells at 0 hours post-treatment, B is agarobiose-treated cells at 0 hours post-treatment, C is agarobiose-untreated cells at 8 hours post-treatment, and D is agarobiose-treated cells at 8 hours post-treatment.

As shown in FIG. 7, it can be seen that at 0 hours post-treatment, both the agarobiose-treated cells (B of FIG. 7) and the untreated cells (A of FIG. 7) were living cells as they show only green fluorescence. On the other hand, it can be seen that at 8 hours post-treatment, most of the agarobiose-treated cells (D of FIG. 7) exhibited red fluorescence unlike the agarobiose-untreated cells (C of FIG. 7). Since red fluorescence indicates cell death, it was confirmed that agarobiose caused the death of *S. aureus*.

<Example 7> Growth Inhibition Experiment of Staphylococci by AHG

The growth inhibition test of Staphylococci was carried out in the same manner as in Example 1, except that AHG (1, 2, 4, and 8 mg/mL) was used instead of the agarooligosaccharide.

Figure 8:
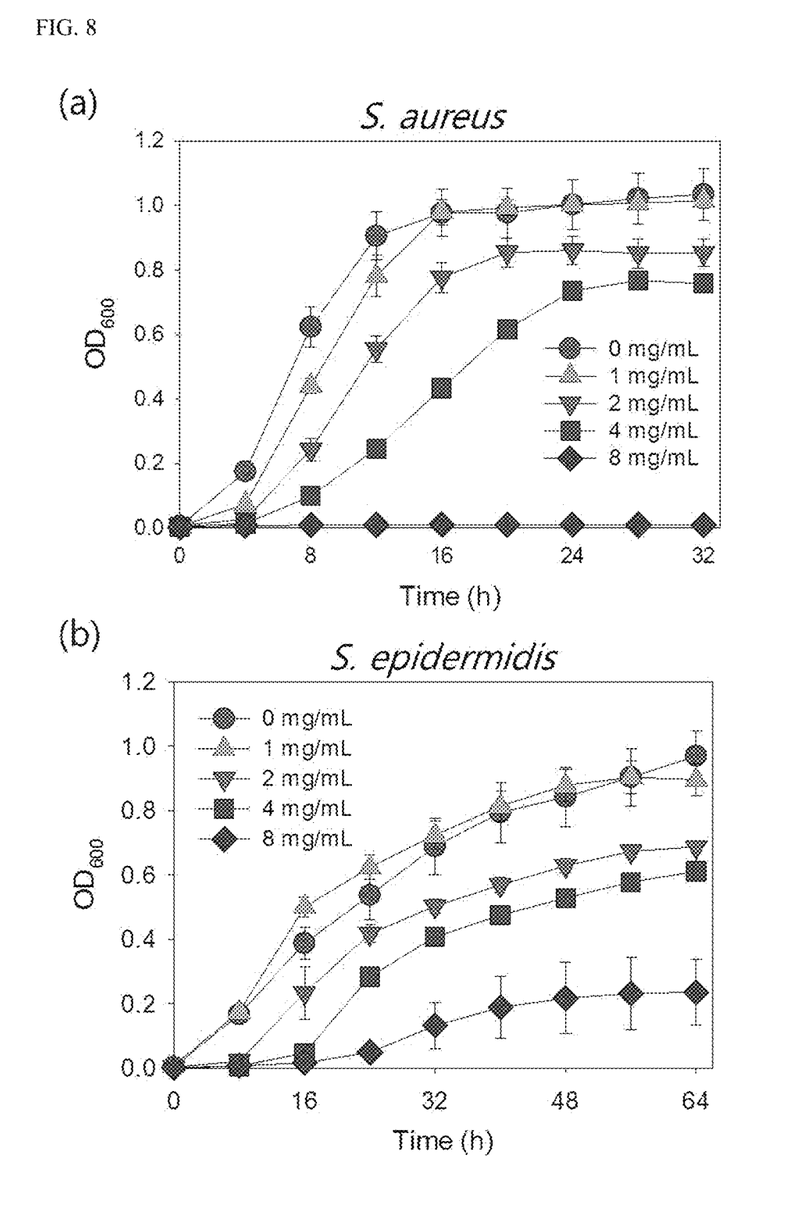
FIG. 8 shows the results of inhibiting the growth of (a) S. aureus and (b) S. epidermidis using AHG.

As shown in FIG. 8, the growth of Staphylococci was more inhibited as the concentration of AHG increased, and was almost completely inhibited at a concentration of 8 mg/mL.

<Comparative Example 1> Growth Inhibition Experiment of Staphylococcusih by Neoagarobiose The growth inhibition test of *S. aureus* was carried out in the same manner as in Example 1, except that neoagarobiose (2.5, 5, 10, and 20 mg/mL) was used instead of the agarooligosaccharide.

Figure 9:
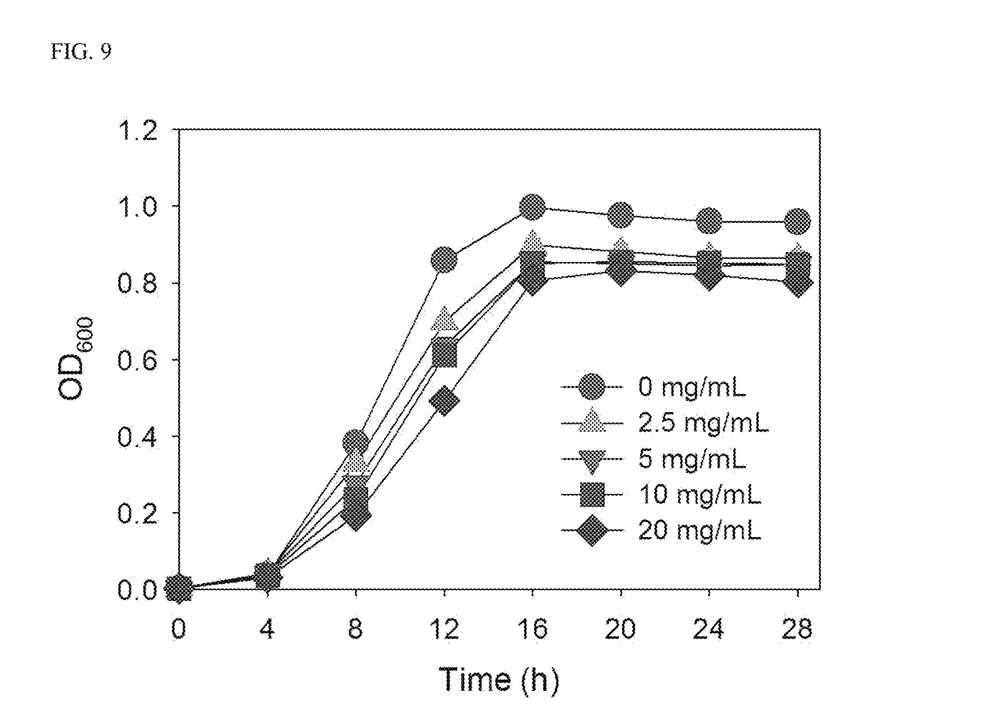
FIG. 9 shows the results of inhibiting the growth of S. aureus using neoagarobiose.

As shown in FIG. 9, the growth of *S. aureus* was not inhibited even at a high neoagarobiose concentration of 20 mg/mL. Therefore, it was confirmed that neoagarobiose had no antibacterial effect against *Staphylococcus*.

<Comparative Example 2> Growth Inhibition Experiment of Staphylococci by Galactose The growth inhibition test of growth of Staphylococci was carried out in the same manner as in Example 1, except that galactose (1, 2, 4, and 8 mg/mL) was used instead of the agarooligosaccharide.

Figure 10:
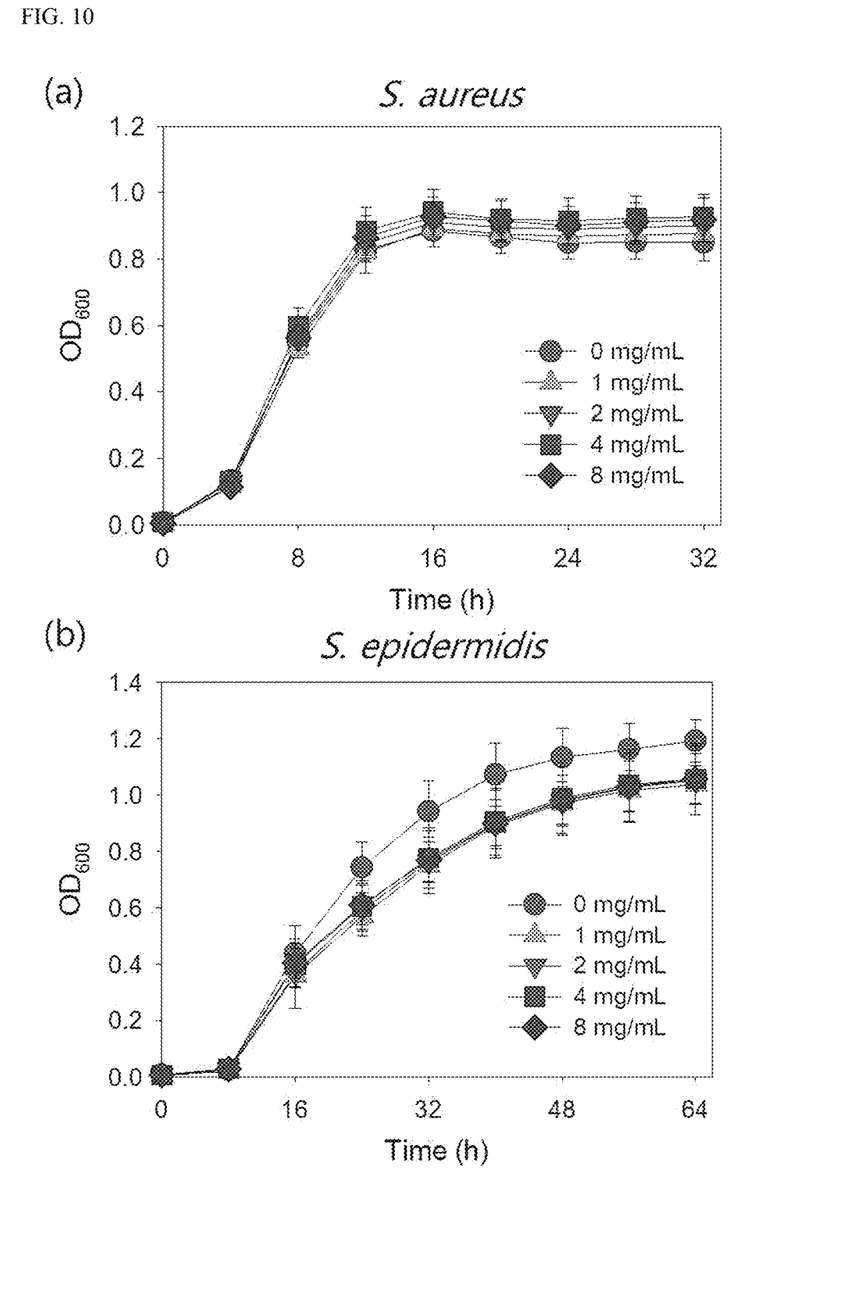
FIG. 10 shows the results of inhibiting the growth of (a) S. aureus and (b) S. epidermidis using galactose.

As shown in FIG. 10, the growth of *S. aureus* was not inhibited at all by galactose. Therefore, it was confirmed that galactose had no antibacterial effect against *Staphylococcus*.

The present invention is applicable to the fields of medicine, food, and cosmetics where an agarooligosaccharide, agarobiose, or AHG, which is derived from agar, is applicable as a material.

What is claimed is:

1. A method of inhibiting the growth of *Staphylococcus* or killing the same, comprising contacting at least one type of *Staphylococcus* with an effective amount of one or more selected from the group consisting of an agarooligosaccharide, and agarobiose,
   wherein the agarooligosaccharide is a mixture of agarobiose, agarotetraose, agarohexaose, and agarooctaose, and
   wherein the *Staphylococcus* is selected from the group consisting of *Staphylococcus aureus*, *Staphylococcus epidermidis*, and *Staphylococcus pyogenes*.

2. A method for treating or alleviating a staphylococcal infectious disease in a subject, comprising administering a pharmaceutically effective amount of one or more selected from the group consisting of an agarooligosaccharide, and agarobiose to the subject in need thereof,
   wherein the agarooligosaccharide is a mixture of agarobiose, agarotetraose, agarohexaose, and agarooctaose, and
   wherein the *Staphylococcus* is selected from the group consisting of *Staphylococcus aureus*, *Staphylococcus epidermidis*, and *Staphylococcus pyogenes*.

3. The method of claim 2, wherein the staphylococcal infectious disease is selected from the group consisting of an abscess, acne, dermatitis, pneumonia, endocarditis, sepsis, osteomyelitis, osteoarthritis, bacteremia, toxic shock syndrome, food poisoning, hyperthermia, edema, mastitis, and enterocolitis caused by an infection by *Staphylococcus aureus*, *Staphylococcus epidermidis*, or *Staphylococcus pyogenes*.

4. A method of inhibiting the growth of *Staphylococcus* or killing the same in an animal subject, comprising administering an effective amount of one or more selected from the group consisting of an agarooligosaccharide, and agarobiose to the animal subject in need thereof,
   wherein the agarooligosaccharide is a mixture of agarobiose, agarotetraose, agarohexaose, and agarooctaose, and
   wherein the *Staphylococcus* is selected from the group consisting of *Staphylococcus aureus*, *Staphylococcus epidermidis*, and *Staphylococcus pyogenes*.

* * * * *